United States Patent

Bradshaw et al.

[11] 4,060,686
[45] Nov. 29, 1977

[54] CEPHALOSPORINS HAVING A 7-(CARBOXY SUBSTITUTED α-ETHERIFIED OXIMINOARYLACETAMIDO) GROUP

[76] Inventors: Janice Bradshaw, 37 Hamilton Road, Harrow, Middlesex; Martin Christopher Cook, 18 Menlove Gardens South, Liverpool 18; Gordon Ian Gregory, 18 The Paddock, Chalfont St. Peter, Buckinghamshire, all of England

[21] Appl. No.: 668,246

[22] Filed: Mar. 18, 1976

Related U.S. Application Data

[63] Continuation-in-part of Ser. No. 533,451, Dec. 16, 1974, abandoned.

[30] Foreign Application Priority Data

Dec. 21, 1973 United Kingdom ............ 59517/73

[51] Int. Cl.$^2$ ............ C07D 501/32; C07D 501/34
[52] U.S. Cl. ............ 544/22; 260/332.2 R; 260/347.4; 544/16; 560/35; 424/246
[58] Field of Search ............ 260/243 C

[56] References Cited

U.S. PATENT DOCUMENTS

| | | | |
|---|---|---|---|
| 3,966,717 | 6/1976 | Cook et al. | 260/243 C |
| 3,971,778 | 7/1976 | Cook et al. | 260/243 C |
| 3,974,153 | 8/1976 | Cook et al. | 260/243 C |

OTHER PUBLICATIONS

Glaxo, Chemical Abstracts, (1975), vol. 83: 179,082S.

Primary Examiner—Nicholas S. Rizzo
Assistant Examiner—David E. Wheeler
Attorney, Agent, or Firm—Bacon & Thomas

[57] ABSTRACT

3-Carbamoyloxymethyl and 3-N-methylcarbamoyloxymethyl cephalosporin antibiotics in which the 7β-acylamido group has the structure

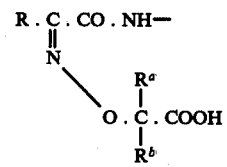

where R is thienyl, furyl or phenyl; $R^a$ is $C_{1-4}$ alkyl, $C_{2-4}$ alkenyl, $C_{3-7}$ cycloalkyl or phenyl, and $R^b$ is hydrogen, carboxy, $C_2$-$C_5$ carbalkoxy or any of the groups designated for $R^a$, or $R^a$ and $R^b$ together with the carbon atom to which they are attached form a $C_{3-7}$ cycloalkylidene or cycloalkenylidene group; exhibit broad spectrum antibiotic activity charcterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of *Escherichia coli, Haemophilus influenzae* and Proteus organisms; and also shown unusually high activity against Pseudomonas organisms.

5 Claims, No Drawings

CEPHALOSPORINS HAVING A 7-(CARBOXY SUBSTITUTED α-ETHERIFIED OXIMINOARYLACETAMIDO) GROUP

CROSS REFERENCE TO RELATED APPLICATION

This application is a continuation-in-part of our U.S. application Ser. No. 533,451 filed Dec. 16, 1974 and now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after J.Amer.-Chem.Soc., 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Pseudomonas organisms are resistant to the majority of existing commercially available antibiotic compounds, and the practical therapeutic applications of aminoglycoside antibiotics such as gentamicin which do exhibit Pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides novel 7β-acylamidoceph-3-em-4-carboxylic acid antibiotics and non-toxic derivatives thereof. These antibiotics have the formula:

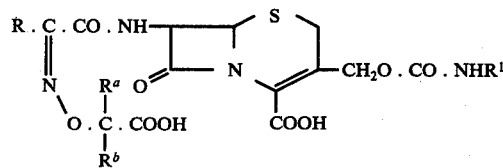

(I)

wherein
R is thienyl, furyl or phenyl,
$R^a$ is $C_1$–$C_4$ alkyl (e.g. methyl, ethyl, n-propyl, isopropyl or butyl) $C_2$–$C_4$ alkenyl (e.g. vinyl or allyl) $C_3$–$C_7$ cycloalkyl (e.g. cyclopropyl cyclobutyl, cyclopentyl or cyclohexyl) or phenyl; $R^b$ is hydrogen, carboxy, $C_2$–$C_5$ carbalkoxy (e.g. ethoxycarbonyl) $C_1$–$C_4$ alkyl (e.g. methyl, ethyl, n-propyl, isopropyl or butyl) $C_2$–$C_4$ alkenyl (e.g. vinyl or allyl) $C_3$–$C_7$ cycloalkyl (e.g. cyclopropyl cyclobutyl, cyclopentyl or cyclohexyl) or phenyl; or $R^a$ and $R^b$ together with the carbon atom to where they are attached form a $C_3$–$C_7$ cycloalkylidene or cycloalkenylidene group (e.g. a cyclobutylidene, cyclopentylidene or cyclohexylidene group) and $R^1$ is hydrogen or methyl.

The compounds are syn isomers or exist as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae*, *serratia marcescens* and *Klebsiella aerogenes*. The compounds have particularly high activity against strains of *Escherichia coli*, *Haemophilus influenzae* and Proteus organisms, e.g. strains of *Proteus morganii* and *Proteus mirabilis* and unusually high activity against Pseudomonas organisms, for example strains of *Pseudomonas aeruginosa*.

The compounds of the invention are defined as having the syn isomeric form as regards the configuration of the group

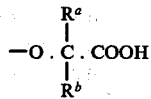

with respect to the carboxamido group. In this specification the syn configuration is denoted structurally as

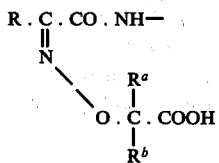

this configuration being assigned on the basis of the work of Ahmad and Spenser reported in Can. J. Chem., 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3–7 (e.g. 5–7) carbon atoms.

A particularly interesting class of cephalosporin antibiotics in accordance with the invention comprises compounds of general formula

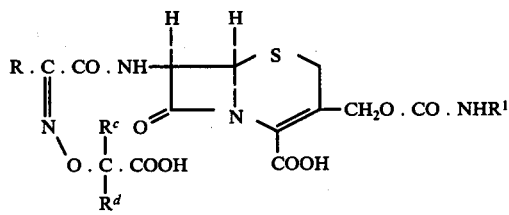

wherein R is thienyl or furyl, $R^c$ represents methyl, ethyl, propyl, allyl or phenyl and $R^d$ represents hydrogen, carboxy or, more preferably, a group as defined for $R^c$; or $R^c$ and $R^d$ together with the carbon atom to which they are attached form a cyclobutylidene, cyclopentylidene or cyclohexylidene group; and $R^1$ is hydrogen or methyl; and non-toxic derivatives thereof.

These compounds exhibit broad spectrum antibiotic activity (including very high activity against strains of *Haemophilus influenzae* and *Proteus* organisms) and high β-lactamase stability and are further characterised by particularly high in vitro activity against Pseudomonas organisms such as strains of *Pseudomonas aeruginosa*.

Especially preferred compounds of the above type, by virtue of their particularly high levels of activity against Proteus and Pseudomonas organisms, include the following:

(6R,7R)-3-carbamoyloxymethyl-7-[2-(2-carboxyprop-2-yloxyimino)-2-(fur-2-yl)acetamido]ceph-3-em-4-carboxylic acid (syn isomer), (6R,7R)-3-carbamoyloxymethyl-7-[2-(1-carboxycyclopent-1-yloxyimino)-2-(fur-2-yl)acetamido]ceph-3-em-4-carboxylic acid (syn isomer), (6R,7R)-3-carbamoyloxymethyl-7-[2-(1-carboxycyclobut-1-yloxyimino)-2-(fur-2-yl)acetamido]ceph-3-em-4-carboxylic acid (syn isomer), and non-toxic derivatives thereof, e.g. alkali metal salts such as the sodium or potassium salts.

The compounds according to the invention may be prepared by any convenient method, for example by techniques analagous to those described in Belgian Pat. No. 783449.

Thus according to one embodiment of the invention we provide a process for the preparation of an antibiotic compound of general formula I as hereinbefore defined or a non-toxic derivative thereof which comprises either (A) condensing a compound of the formula

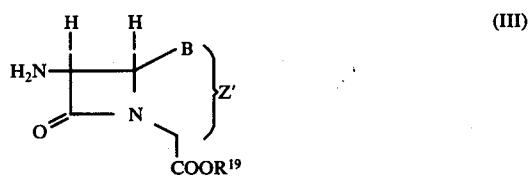

[wherein B is >S or >S→O (α- or β-); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms) or a symmetrical or mixed anhydride group derived from an appropriate acid; and Z' is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

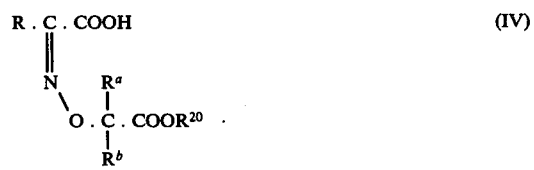

(wherein R, $R^a$ and $R^b$ are as hereinbefore defined and $R^{20}$ is a carboxyl blocking group, e.g. a group as hereinbefore defined in connection with $R^{19}$); or (B), reacting a compound of the formula

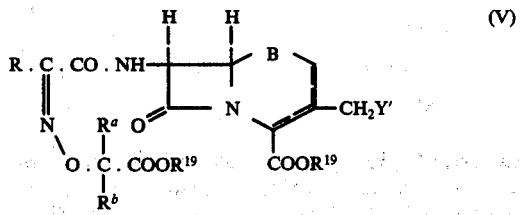

(wherein B,R,$R^a$ and $R^b$ are as hereinbefore defined; each $R^{19}$ may independently represent hydrogen or a carboxyl blocking group; Y' is a replaceable residue of a nucleophile, e.g. a hydroxy group, a halogen atom such as chlorine, bromine or iodine; and the dotted line bridging the 2-, 3- and 4-positions indicates that the compound is a ceph-2-em or ceph-3-em compound) with a nucleophile e.g. sodium acetate; whereafter, if necessary and/or desired in each instance, any of the following reactions (C) in any appropriate sequence, are carried out:

i. conversion of a $\Delta^2$ isomer into the desired $\Delta^3$ isomer, ii. reduction of a compound wherein B is $>$S$\rightarrow$0 to form a compound wherein B is $>$S, iii. carbamoylation of a 3-hydroxymethyl compound to form an unsubstituted or substituted 3-carbamoyloxymethyl compound, and iv. removal of carboxyl blocking groups;

and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (IV) or a salt thereof with a halogenating agent e.g. phosphorus pentachloride, thionyl chloride or oxalyl chloride. Treatment of the sodium, potassium or triethylammonium salt of the acid (IV) with oxalyl chloride is advantageous in that under these conditions isomerisation is minimal.

Acylations employing acid halides may be effected in aqueous and non-aqueous reaction media, conveniently at temperatures of from −50° to +50° C, preferably −20° to +30° C, if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula IV may themselves be used as acylating agents in the preparation of compounds of formula I. Acylations employing acids (IV) are desirably conducted in the presence of a condensation agent, for example a carbodiimide such as N,N'-diethyl-, dipropyl- or diisopropylcarbodiimide, N,N'-dicyclohexylcarbodiimide or N-ethyl-N'-γ-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula IV such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

Carbamoylation of 3-hydroxymethyl compounds may be effected by conventional methods. Thus, for example, a 3-hydroxymethyl cephalosporin may be reacted with an isocyanate of formula $R^e$.NCO (wherein $R^e$ represents a labile substituent group or an alkyl group) to give a compound containing a 3-position substiuent having the formula —CH$_2$O.CONHR$^e$ (wherein $R^e$ has the above defined meaning). Where $R^e$ is a labile substituent this substituent may if desired subsequently be cleaved, e.g. by hydrolysis, to form a 3-carbamoyloxymethyl group. Labile groups $R^e$ which are readily cleavable upon subsequent treatment include chlorosulphonyl and bromosulphonyl; halogenated lower alkanoyl groups such as dichloroacetyl and trichloroacetyl; and halogenated lower alkoxycarbonyl groups such as 2,2,2-trichloroethoxycarbonyl. These labile $R^e$ groups may generally be cleaved by acid or base catalysed hydrolysis (e.g. by base catalysed hydrolysis using sodium bicarbonate).

Another carbamoylating agent of use in the carbamoylation of 3-hydroxymethyl cephalosporins is cyanic acid, which is conveniently generated in situ from, for example, an alkali metal cyanate such as sodium cyanate, the reaction being facilitated by the presence of an acid, e.g. a strong organic acid such as trifluoroacetic acid. Cyanic acid effectively corresponds to a compound of formula $R^e$.NCO wherein $R^e$ is hydrogen, and therefore converts 3-hydroxymethyl cephalosporin compounds directly to their 3-carbamoyloxymethyl analogues.

3-Hydroxymethyl cephalosporins for use in the above carbamoylation reactions may, for example, be prepared by the methods described in British Pat. No. 1,121,308 and Belgian Pat. Nos. 783,449 and 841,937.

$\Delta^2$-Cephalosporin ester derivatives obtained in accordance with the process of the invention may be converted into the corresponding $\Delta^3$ derivative by, for example, treatment of the $\Delta^2$ ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>$S$\rightarrow$O this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-$d_6$ solutions of syn compounds of Formula I exhibit the doublet for the amide NH at a lower field than do similar solutions of the corresponding anti-isomers. These factors may be employed in monitoring reactions.

Acids (IV) may be obtained by reacting a glyoxylic acid of formula

R.CO.COOH     (VI)

(where R has the above-defined meaning) of an ester thereof with a hydroxylamine derivative of formula

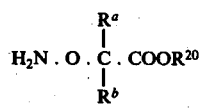

(VII)

(where $R^a$, $R^b$ and $R^{20}$ have the above-defined meanings). The resulting acid or ester may be separated into its syn and anti isomers by, for example, crystallisation, chromatography or distillation, whereafter ester derivatives may be hydrolysed to yield the corresponding acid.

Acids (IV) may also be prepared by etherification of an acid of formula

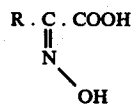

(VIII)

(where R has the above-defined meaning), e.g. by reaction with a compound of general formula

(IX)

(wherein $R^a$, $R^b$ and $R^{20}$, are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction.

Acids of formula IV and acylating agents derived therefrom (e.g. acyl halides such as the chloride) are novel and comprise a feature of the present invention.

Derivatives of the compounds of the invention in which the carboxy substituent of the 7β-acylamido side chain is substituted by a carboxyl blocking group are also new and comprise a feature of the invention. These monoester derivatives, which may be represented by the general formula

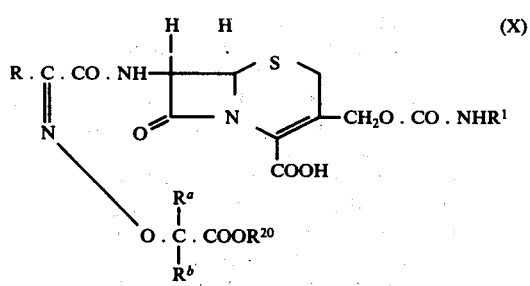

(X)

(wherein R, $R^1$, $R^a$ and $R^b$ are as hereinbefore defined and $R^{20}$ is a carboxyl blocking group such as t-butyl or diphenylmethyl), are of value as intermediates in the preparation of antibiotic compounds of general formula I. The compounds (X) may themselves exhibit antibiotic activity, although generally at a very low level when compared to corresponding compounds (I).

Carboxyl blocking groups $R^{20}$ and, where appropriate, $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maize-starch; calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g., 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in ° C. The structure of the products were verified by p.m.r. spectroscopy (Preparations and Examples) and i.r. spectroscopy (Examples only).

PREPARATION 1

2-(2-t-Butoxycarbonylprop-2-yloxyimino)-2-(fur-2-yl)acetic acid (syn isomer)

A solution of 2-(fur-2-yl)-2-hydroxyiminoacetic acid (syn isomer) (14.1g) in dimethyl sulphoxide (100ml) was added all at once to a magnetically stirred solution of potassium t-butoxide (22.4g) in dimethyl sulphoxide (400ml), the reaction mixture being maintained under an atmosphere of dry nitrogen. A gel was formed which, on stirring, became a finely divided, yellow solid. Stirring was continued for one hour, and then a solution of t-butyl 2-bromo-2-methylpropionate (24.0g) in dimethyl sulphoxide (50ml) was added over one hour to the reaction mixture at room temperature. After addition was complete. the resulting solution was stirred for a further hour. The reaction was poured into ice-water (1.5 liters) and acidified under ether (500ml) to pH 1.8 with concentrated hydrochloric acid. The two layers were separated, and the aqueous layer was extracted with more ether. The combined ether extracts were washed once with water, then extracted with aqueous sodium bicarbonate solution. The combined alkaline extracts were acidified under ether to pH 1.8 with concentrated hydrochloric acid, and the acid solution was extracted further with ether. The combined ether extracts were washed (water, saturated brine), dried, and concentrated to a yellow oil, which crystallised under high vacuum (22.41g, 83%), $\lambda_{max}$(EtOH) 272.5nm ($\epsilon$15,400).

The above solid (22.4g) was crystallised from carbon tetrachloride (25ml) to give the title compound (16.42g, 61%), m.p. 72.5°–74.2° (73.0°).

PREPARATIONS 2 and 3

Method

The dipotassium salt of 2-(fur-2-yl)-2-hydroxyiminoacetic acid (syn isomer) was generated under an atmosphere of dry nitrogen and alkylated with the appropriate halo-t-butyl ester as described in Preparation 1. The products were isolated by pouring into water, acidifying, and extracting in the conventional manner.

TABLE 1

| Preparation | | m.p. | $\lambda_{max}$,nm |
|---|---|---|---|

TABLE 1-continued

| No. | R^q | R^20 | °C | (solvent) | ε |
|---|---|---|---|---|---|
| 2 | 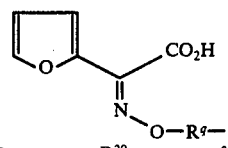 | —C(CH₃)₃ | 106.8–107.3° | 277.5(pH6 buffer) | 15,100 |
| 3 | 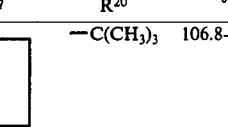 | " | 113–114° | 278(pH6 buffer) | 17,200 |

| Preparation No. | τ values d₆-DMSO | |
|---|---|---|
| | R^q | R^20 |
| 2 | 8.03; 8.30 | 8.63 |
| 3 | 7.4–8.3 | 8.59 |

PREPARATION 4

2-(2-tert-Butoxycarbonylprop-2-yloxyimino)-phenylacetic acid (syn isomer)

To a well-stirred solution of potassium tert-butoxide (449mg, 4mmole) in dry DMSO (10ml) was added in one portion a solution of syn-2-hydroxyiminophenylacetic acid (330mg, 2mmole) in DMSO (5ml). The mixture was stirred for 45 min, then tert-butyl α-bromoisobutyrate (446mg, 2mmole) in DMSO (5ml) was added. The mixture was stirred for 3.5hr at room temperature, then poured into ice-water (150ml). Ether (125 ml) was added and the pH was adjusted to 1.5 (conc. HCl). The aqueous layer was again extracted with ether, and the ether extracts washed with water and extracted into saturated sodium bicarbonate solution. The extract was acidified (pH 1.5) and extracted with ether. The ether layer was separated and washed with water and dried (Na₂SO₄). Evaporation left an oil, which later solidified. The product was dissolved in methylene chloride (8ml) and filtered, and the filtrate was evaporated, leaving an off-white solid (310mg, 50%), m.p. 102°–105°, $\lambda_{max}$ (58994, EtOH) 253.5nm (ε 12,700).

EXAMPLE 1 a. (6R,7R)-3-carbamoyloxymethyl-7-[2-t-butoxycarbonylcyclobut-1-yl oxy-imino-2-(fur-2-yl)acetamido]ceph-3-em-4-carboxylic acid (syn isomer)

Oxalyl chloride (0.30 ml) was added at 5° to a stirred solution of 2-t-butoxycarbonylcyclobut-1-yloxyimino-2-(fur-2-yl) acetic acid (syn isomer) (0.930 g) in dry dichloromethane (23 ml) containing triethylamine (0.45 ml) and dimethylformamide (2 drops). The solution was stirred at 5° for 45 mins. and was then evaporated to dryness at 5°. The residue was suspended in acetone (25 ml) and was added over 30 minutes to a stirred, ice-cooled solution of (6R, 7R)-3-carbamoyloxymethyl-7-aminoceph-3-em-4-carboxylic acid (0.90 g) in water (40 ml) and acetone (30 ml) containing sodium bicarbonate (0.83 g). The reaction mixture was stirred for one hour, whereafter the acetone was evaporated under reduced pressure. The residue was acidified to pH 1.5, and this mixture was extracted with ether. The combined extracts were washed (water, saturated brine), dried, and evaporated to give the title compound (1.56 g, 92.5%) as a white foam, τ(DMSO-d₆) values include 7.57 and 8.10 (m.cyclobutyl); 8.58 (t-butyl); 0.34 (d.J8H$_z$, NH) and 4.14 (dd, 7-H̲).

b. (6R, 7R)-3-carbamoyloxymethyl-7-[2-carboxycyclobut-1-yl oxyimino-2-(fur-2-yl)-acetamido]ceph-3-em-4-carboxylic acid, disodium salt (syn isomer)

A solution of (6R, 7R)-3-carbamoyloxymethyl-7-[2-t-butoxycarbonylcyclobut-1-yloxyimino-2-(fur-2-yl) acetamido]ceph-3-em-4-carboxylic acid (syn isomer) (1,13 g) and anisole (1 ml) in trifluroacetic acid (5 ml) was kept at ambient temperature for 15 minutes, then the trifluoroacetic acid was removed in vacuo. The residue was dissolved in ethyl acetate (30 ml), and extracted with aqueous sodium bicarbonate (4 × 10 ml). The combined alkaline extracts were washed with ethyl acetate and acidified to pH 1.3 under ethyl acetate. The acid mixture was extracted with ethyl acetate, and the combined ethyl acetate extracts were washed (water, saturated brine), dried, and evaporated to give the dicarboxylic acid corresponding to the title compound (0.99 g, 98%), τ (d₆ - DMSO) values include 0.34 (d, J 8Hz, NH), 4.12 (dd, 7-H̲), and 7.56, 8.10 (m. cyclobutyl).

This di-acid (560 mg) in acetone 7.5 ml was neutralised with a solution of sodium 2-ethylhexanoate (366 mg) in acetone (3.5 ml). The mixture was stirred for a few minutes, then the precipitated solid was filtered off, washed with acetone and ether, and dried to give the title compound (630 mg), λ max (pH 6 buffer) 277.5 nm. (ε 16,946).

EXAMPLES 2 and 3

General Procedure for the Preparation of (6R, 7R)-7-(2-Aryl-2-carboxy-R^q-oxyiminoacetamido)-3-(substituted) ceph-3-em-4-carboxylic Acids (sun-isomers) and/or their Salts Method A Following the procedure described in Example 1, a solution of the appropriate 2-aryl-2-t-butoxycarbonyl-R^q-oxyiminoacetic acid (syn-isomer) (1 equiv) in methylene chloride optionally containing a few drops of N,N-dimethylformamide and triethylamine (1 equiv) was treated with oxalyl chloride (1 equiv) at 0°–5° for ca.1 hour. The mixture was then evaporated to dryness. The residue was suspended or dissolved in acetone and added to a stirred ice-cold solution of (6R, 7R)-3-(substituted methyl)-7-aminoceph-3-em-4-carboxylic acid (1-1,2equiv) in water or a mixture of acetone and water containing sodium hydrogen carbonate (2-2.5 equiv). The reaction mixture was stirred for 0.5 - 2.5 hours, allowing the temperature to rise to room temperature, whereafter the acetone was removed under reduced pressure. The pH was adjusted to 1.5 - 2.0 and the product extracted into ethyl acetate (alternatively ether or methylene chloride may be used). The organic layer was washed with temperature, whereafter the acetone was removed under reduced pressure. The pH was adjusted to 1.5 - 2.0 and the product extracted into ethyl acetate (alternatively ether or methylene chloride may be used). The organic layer was washed with water and/or saturated brine, dried and evaporated to give the corresponding (6R, 7R)-3-(substituted methyl)-7-(2-aryl-2-t-butoxycarbonyl-R$^q$-oxyiminoacetamido)ceph-3-em4-carboxylic acid (syn-isomer) which was characterised by optical rotation and/or by spectroscopy.

The t-butyl esters were deprotected by treating with trifluoracetic acid containing anisole at room temperature for at least 5 minutes. The reaction mixture was evaporated in vacuo and the product isolated by trituration or by distributing between ethyl acetate (or ether) and an aqueous solution of sodium hydrogen carbonate, separating the aqueous extracts, acidifying these extracts under ethyl acetate and isolating the title dicarboxylic acid in the usual way. The products are listed in Table 2.

Method B

As Method A except that the dicarboxylic acid was converted into its disodium salt by treating a solution of the acid in acetone with a solution of sodium 2-ethylhexanoate in acetone. The precipitated disodium salt was washed and dried. The products are listed in Table 2.

EXAMPLES 4 - 6

General Procedure for the Preparation of (6R, 7R)-7-[2-carboxy-R$^a$-oxyimino-2-(R$^p$) acetamido]-3-(substituted)-ceph-3-em-4-carboxylic acids (syn isomers) using Dicyclohexylcarbodiimide i. To a solution of a diphenylmethyl (6R, 7R)-7-amino-3-(substituted)ceph-3-em-4-carboxylate (1 equiv) and dicyclohexylcarbodiimide (1-1.3 equiv) in dry methylene chloride was added at 0°-25° a solution of the appropriate 2-t-butoxycarbonyl-R$^q$-oxyimino-2-(R$^p$)acetic acid (syn isomer) (1-1.15 equiv) in dry methylene chloride. After stirring for 0.5-5.0 hours the dicyclohexylurea was removed by filtration and the filtrate was evaporated. The residue in ethyl acetate or methylene chloride was washed successively with aqueous sodium bicarbonate, water and brine, dried and evaporated. The diester was purified by chromatography on silica or, after decolourisation with charcoal, by trituration or crystallisation. The product was characterised by its p.m.r. spectrum and by thin layer chromatography.

When the 7-amino starting material was available as an acid addition salt the free base was liberated by shaking with a mixture of ethyl acetate (or methylene chloride) and an excess of an aqueous solution of sodium bicarbonate. After washing with water and brine the organic layer was evaporated to dryness and the free amine used as described above.

ii. Method A. The intermediate diesters so derived were deprotected by dissolving in a mixture of trifluoracetic acid (3–10 ml/1 g of diester) and anisole (0.8 –12 ml/1 g of diester) and left at between 0° and room temperature for between 5 minutes and 2.5 hours. The mixture was concentrated under reduced pressure and added to a mixture of ethyl acetate or ether and excess aqueous sodium bicarbonate, and the aqueous layer was washed with ethyl acetate. The aqueous phase was covered with ethyl acetate and acidified to pH 1-2 with hydrochloric acid. The organic layer was washed, dried and evaporated to give the required dicarboxylic acid.
ii. Method B.

TABLE 2

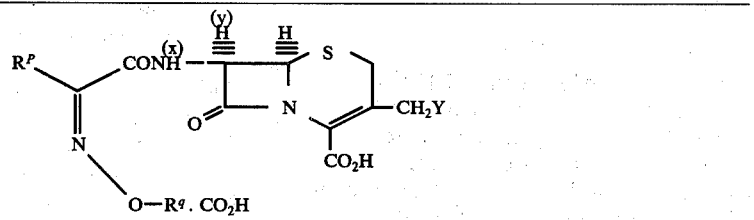

| Ex. No. | R$^p$ | R$^q$ | Y | Salt | Method | [α]$_D$ (solvent) | λ$_{max}$ nm (pH6 buffer) | ε | β-lactam ν$_{max}$ cm$^{-1}$ (Nujol) |
|---|---|---|---|---|---|---|---|---|---|
| 2 | furyl | cyclopentyl | —OCONHCH$_3$ | — | A | +41.2° (DMSO) | 277 | 17,850 | 1780 |
| 3 | furyl | >C(CH$_3$)$_2$ | —OCONH$_2$ | disodium | A | +44° (H$_2$O) | 274.5 | 14,950 | 1773 |

| Ex. No. | τ* values for d$_6$-DMSO at 100 MHz | | |
|---|---|---|---|
| | x | y | R$^q$ |
| 2 | 0.48 | 4.18 | 7.95; 8.3 |
| 3 | 0.44 | 4.15 | 8.52 |

In some cases where treatment with trifluoracetic acid was insufficient to complete deprotection the intermediate monoester (usually the t-butoxycarbonyl group was cleaved more slowly than the diphenylmethoxycarbonyl group) was retreated with trifluoracetic acid and anisole and the diacid isolated as described above.

The properties of the reaction products are listed in Table 3.

TABLE 3

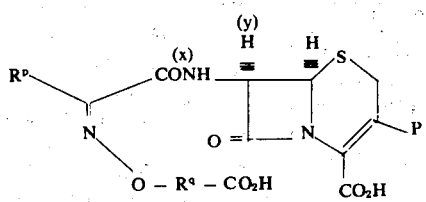

| Ex. No. | $R^p$ | $R^q$ | P | Method | $[\alpha]_D$ (solvent) | $\lambda_{max}$, nm (solvent) | $\Sigma$ | β-lactam $\nu_{max}$ cm$^{-1}$ (Nujol) |
|---|---|---|---|---|---|---|---|---|
| 4 | 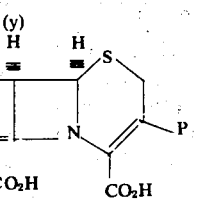 | \C(CH$_3$)$_2$ / | —CH$_2$OCONH$_2$ | B | +62° (EtOH) | 275 (pH 6 buffer) | 14,850 | 1775 |
| 5 | (furan) | (cyclopentyl) | —CH$_2$OCONH$_2$ | A | +52° (EtOH) | 274.5 (pH 6 buffer) | 15,700 | 1778 |
| 6 | Ph | \C(CH$_3$)$_2$ / | —CH$_2$OCONH$_2$ | A | 35.5° (DMSO) | 257 (EtOH) | 16,000 | 1784 |

| Ex. No. | τ values for d$_6$-DMSO at 100 MHz | | |
|---|---|---|---|
| | x | y | $R^q$ |
| 4 | 0.24 | 4.14 | 8.52 |
| 5 | 0.45 | 4.14 | 7.9; 8.25 |
| 6 | 0.38 | 4.02 | 8.47 |

EXAMPLE A

This example illustrates the formulation of a pharmaceutical composition.

Dry Powder for Injection

Sterile (6R, 7R)-3-carbamoyloxymethyl-7-[2-(2-carboxy cyclobut-1-yloxyimino)-2-(fur-2-yl)acetamido] ceph-3-em-4-carboxylate disodium salt (syn-isomer) is filled into glass vials, the claimed contents of each container being 500 mg or 1.00 g of the antibiotic as desired. Filling is carried out asceptically under a blanket of nitrogen. The vials are closed using rubber discs or plugs held in position by aluminium sealing rings, thereby preventing gaseous exchange or ingress of microorganisms. The product would be intended for reconstitution with water for injections or other suitable sterile vehicle shortly before administration.

We claim:

1. A cephalosporin antibiotic of the formula:

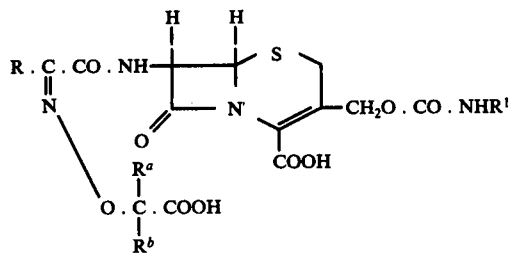

wherein
R is thienyl, furyl or phenyl;
$R^a$ and $R^b$ together with the carbon atom to which they are attached form a cyclobutylidene, cyclopentylidene or cyclohexylidene group; and
$R^1$ is hydrogen or methyl;
or a physiologically acceptable salt, ester, or 1-oxide thereof.

2. The compound of claim 1 which is (6R, 7R)-3-carbamoyloxymethyl-7-[2-(1-carboxycyclobut-1-yloxyimino)-2-(fur-2-yl)acetamido]ceph-3-em-4-carboxylic acid (syn isomer).

3. The compound of claim 1 which is (6R, 7R)-3-carbamoyloxymethyl-7-[2-(1-carboxycyclopent-1-yloxyimino)-2-(fur-2-yl)acetamido]ceph-3-em-4-carboxylic acid (syn isomer).

4. The compound of claim 1 which is (6R, 7R)-7-[2-(1-carboxycyclopent-1-yloxyimino)-2-(fur-2-yl)acetamido]-3-N-methylcarbamoyloxymethylceph-3-em-4-carboxylic acid (syn isomer).

5. A cephalosporin antibiotic of the formula:

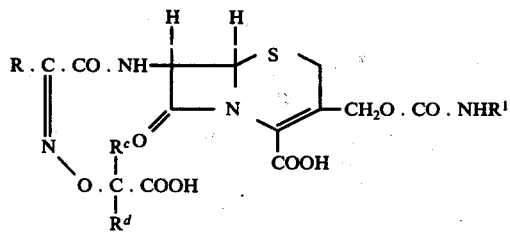

wherein R is thienyl or furyl; $R^c$ and $R^d$ together with the carbon atom to which they are attached form a cyclobutylidene, cyclopentylidene or cyclohexylidene group; and $R^1$ is hydrogen or methyl; or a physiologically acceptable salt or 1-oxide thereof.

* * * * *